United States Patent [19]

De Marco et al.

[11] Patent Number: 4,529,586

[45] Date of Patent: Jul. 16, 1985

[54] HAIR CONDITIONING COMPOSITION AND PROCESS

[75] Inventors: Richard De Marco, Danbury; Joseph Varco, Fairfield; Leszek J. Wolfram, Stamford; Michael Wong, Easton, all of Conn.

[73] Assignee: Clairol Incorporated, New York, N.Y.

[21] Appl. No.: 362,201

[22] Filed: Mar. 26, 1982

Related U.S. Application Data

[63] Continuation-in-part of Ser. No. 165,468, Jul. 11, 1980, abandoned, which is a continuation-in-part of Ser. No. 68,986, Aug. 23, 1979, abandoned.

[51] Int. Cl.$^3$ .................... A61K 7/06; A61K 3/695
[52] U.S. Cl. .......................... 424/70; 514/63
[58] Field of Search ............................ 424/70

[56] References Cited

U.S. PATENT DOCUMENTS

| | | | |
|---|---|---|---|
| 3,142,623 | 7/1964 | Zviak et al. | 424/70 |
| 3,261,838 | 7/1966 | Wakeman et al. | 260/286 |
| 3,290,304 | 12/1966 | Kalopissis et al. | 260/247.2 |
| 3,366,673 | 1/1968 | Wakeman et al. | 260/501.15 |
| 3,683,939 | 8/1972 | Johnsen et al. | 132/7 |
| 3,715,428 | 2/1973 | Quasius et al. | 424/47 |
| 3,733,312 | 5/1973 | Deetman | 260/78.5 T |
| 3,876,760 | 4/1975 | Nersesian et al. | 424/70 |
| 3,885,577 | 5/1975 | Edelberg et al. | 132/7 |
| 3,906,091 | 9/1975 | Zviak et al. | 424/70 |
| 3,910,862 | 10/1975 | Barabas et al. | 260/79.3 MU |
| 3,914,403 | 10/1975 | Valan | 424/47 |
| 3,917,815 | 11/1975 | Kalopissis et al. | 424/70 |
| 3,954,846 | 5/1976 | Grignard | 260/501.15 |
| 3,954,960 | 5/1976 | Valan | 424/47 |
| 3,958,581 | 5/1976 | Abegg et al. | 132/7 |
| 3,959,461 | 5/1976 | Bailey et al. | 424/70 |
| 3,959,463 | 5/1976 | Nersesian et al. | 424/70 |
| 3,980,091 | 9/1976 | Dasher | 424/71 |
| 3,980,769 | 9/1976 | Ghilardi et al. | 424/70 |
| 3,992,336 | 11/1976 | Faucher et al. | 132/7 |
| 4,001,394 | 1/1977 | Fogel et al. | 424/70 |
| 4,011,878 | 3/1977 | Abegg et al. | 132/7 |
| 4,035,478 | 7/1977 | Mullen | 424/70 |
| 4,038,294 | 7/1977 | Conner et al. | 424/70 X |
| 4,041,150 | 8/1977 | Karjala | 424/71 |
| 4,052,331 | 10/1977 | Dumoulin | 424/184 |
| 4,061,602 | 12/1977 | Oberstar et al. | 252/547 |
| 4,069,347 | 1/1978 | McCarthy et al. | 424/70 |
| 4,136,250 | 1/1979 | Mueller et al. | 424/184 |
| 4,172,887 | 10/1979 | Vanlerberghe | 424/70 |
| 4,783,917 | 1/1980 | Jwao et al. | 424/70 |

FOREIGN PATENT DOCUMENTS

| | | | |
|---|---|---|---|
| 1030518 | 5/1958 | Fed. Rep. of Germany | 424/78 |
| 2808830 | 9/1978 | Fed. Rep. of Germany | 424/70 |
| 7607314 | 1/1977 | Netherlands | 424/70 |

*Primary Examiner*—Dale R. Ore
*Attorney, Agent, or Firm*—Gabriel P. Katona

[57] ABSTRACT

A hair conditioning composition containing an amino functional silicone polymer in aqueous emulsion such as amodimethicone, and an effective amount for increasing the combability of hair of a cationic surfactant-emulsifier containing at least one long chain fatty acid residue which has between 12 and 18 carbon atoms, and an effective amount for increasing the combability of hair and for improving the durability of the conditioning effect of at least one cationic polymer in an aqueous carrier. The process of the invention involves the application of the aforementioned conditioning composition before or after shampooing whereby the durability of the conditioning effect is further enhanced.

6 Claims, No Drawings

HAIR CONDITIONING COMPOSITION AND PROCESS

This is a continuation-in-part of application Ser. No. 165,468 filed on July 11, 1980 which is a continuation-in-part of Ser. No. 68,986 filed on Aug. 23, 1979, both now abandoned.

BACKGROUND OF THE INVENTION

Silicone polymers have been used in the past for the conditioning of hair. The conditioning effect of the prior art silicones is of a limited durability and extent and the ability of the silicone to deposit on the hair is also quite limited.

BRIEF SUMMARY OF THE INVENTION

We discovered that an enhanced hair conditioning effect of long duration can be obtained by employing a cationic aqueous emulsion of an amino-functional silicone polymer in combination with a cationic surfactant-emulsifier and a cationic polymer in an aqueous carrier.

DETAILED DESCRIPTION

Silicone polymers in the prior art know to be deposited on hair from an aqueous emulsion. The term "emulsion" as used herein is also intended to cover all disperse systems which generally behave similarly to emulsions. The surface of the hair is, depending on its condition and pH, more or less hydrophilic. Therefore, deposition of the silicone on the hydrophilic hair surface is quite limited. We have found that the incorporation of a relatively small amount of a water soluble cationic polymer in the composition of the present invention results in a double benefit. We believe that one benefit derives from the fact that the cationic polymer which is substantive to the hair primes the hydrophylic surface of the hair to make it less hydrophilic, which then assists in breaking up of the emulsion and promotes the deposition of the hydrophobic silicone onto the hair. The further benefit of the cationic polymer derives from the discovery that upon the shampooing of the hair with an anionic surfactant the cationic polymer forms in situ on the hair a conditioning complex which will further improve the durability of the conditioning effect to last through several shampoos. The shampooing with the anionic shampoo can take place before or after treatment with the conditioner of the present invention.

As some cationic polymers can perform the priming function better than can enter into an ionic interaction with the anionic shampoo thus further to improve the durability of the conditioning effect, in some embodiments of the present invention more than one cationic polymer can be employed.

As the amino functional silicone polymer of the present invention one of the most suitable compounds is amodimethicone, sold by Dow-Corning Corporation in the form of its aqueous cationic emulsion under the trade name Silicone Emulsion No. 929. The name amodimethicone, as other names used in this application, as far as possible, are the CTFA adopted names as shown in the CTFA Cosmetic Ingredient Dictionary (published by The Cosmetic, Toiletry and Fragrance Association, Inc., Washington, D.C. in 1977). Amodimethicone has the formula:

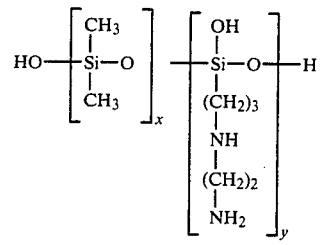

where x and y are cardinal numbers depending on molecular weight and the weight average molecular weight is approximately between 5,000 and 100,000. Silicone Emulsion No. 929 is a cationic aqueous emulsion emulsified with a cationic surfactant such as a long chain fatty acid quaternary ammonium compound such as stearalkonium chloride or tallowtrimonium chloride, and normally also an emulsifying assistant such as an ethoxylated alkyl phenol, for example, nonoxynol-10. Another suitable amino functional silicone polymer is sold by Dow-Corning Corp. under the trade name Q4-656. Generally any cationic surfactant will be satisfactory, having at least one long chain fatty acid residue, said residue containing between 12 and 18 carbon atoms.

We discovered that the usual concentration of from about 0.1 to about 0.2% by weight, based on the entire composition, of the cationic surfactant employed in the commercial emulsion does not produce sufficiently good results, because there is some residual static in the hair (i.e. flyaway). This can be reduced by the further addition of from about 0.01% to about 0.2% by weight of the cationic surfactant, in the given case stearalkonium chloride. The addition of more than 0.2% of that particular surfactant to make the concentration of the cationic surfactant from about 0.11% to about 0.4% by weight resulted in an improvement in reducing static retention, but it was observed that increasing the concentration of the cationic surfactant above a point begins to decrease the overall conditioning efficiency of the composition.

Conditioning efficiency can be determined by measuring and comparing the ease of combability of the treated hair with that of the untreated hair. The apparatus and the measuring technique are described in the article by M. Garcia et al. in 27 J. Soc. Cosmetic Chemists, pp. 379-398 (Sept. 1976), entitled "Combability measurements on Human Hair, which is incorporated herein by reference thereto. The static charge retention of hair can be simply determined by the use of an electroscope.

Conditioning efficiency will depend on the particular hair that is treated as well as on the identity of the specific ingredients that are employed. Therefore, it is not possible to state explicit concentration ranges that are applicable to all variables. Hence the term "effective amount", as used throughout the specification and the claims, is intended to cover a range of concentrations for a stated ingredient within which the composition works as intended for the stated purpose. Thus the effective amounts for the ingredients of the present invention can be easily determined by routine experimentation as guided by this disclosure.

Another feature of the present invention is the presence of an effective amount of a cationic polymer. We found that in the case of using e.g. quaternium-40 as the cationic polymer on a given hair and when 0.2% by weight of stearalkonium chloride was added to the aqueous silicone emulsion which already contained 0.1% tallowtrimonium chloride, the use of over 0.3% of the above cationic polymer resulted in increasingly significant static retention by that hair variety. Therefore, the effective amount of the cationic polymer that is to be employed under given conditions can also be determined by routine experimentation. It would be expected in the particular component system which we tested in greatest detail that between 0.05% to about 0.5% by weight based on the total composition of cationic polymer will generally suffice.

An important feature of the present invention is the durability of the conditioning effect. Whereas hair conditioners in the prior art provided satisfactory conditioning until the next shampooing which then removed the conditioning effect, the effect that is obtained by the composition and the process of the present invention is durable. This means that the hair remains conditioned through several subsequent shampoos, as measured by the reduction of combing force, even as many as 3-5 such shampoos.

Cationic polymers that have been found to be particularly useful in the compositions of the present invention are exemplified below.

Quaternium-40 Sold by Merck & Co. under the trademark MERQUAT-100 is said to be constituted of repeated units of the moiety:

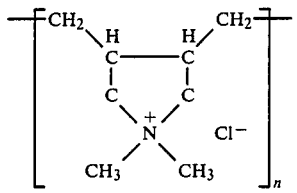

where n is cardinal number proportional to the molecular weight of the polymer.

Quaternium-41 sold by Merck & Co. under the name Merquat-550 is said to be a copolymer of dimethyldiallylammonium chloride (the monomer of quaternium-40) with acrylamide.

polyquaternium-1, a polymeric quaternized dimethylbutenylammonium chloride terminated with quaternized ethanolamine groups, sold by Onyx Chemicals Co. under the name Onamer M hereinafter referred to as "Onamer", and said to have the formula:

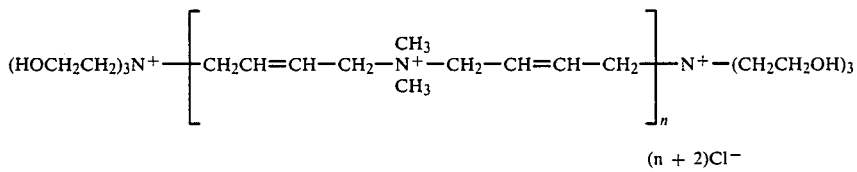

(n + 2)Cl⁻ where n is a cardinal number which is proportional to molecular weight.

quaternized poly-4-vinyl pyridine, hereinafter referred to as "QPVP", which is believed to be constituted from repeating units of the moiety:

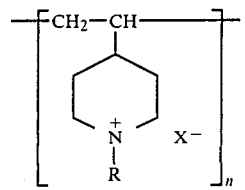

where n is a cardinal number which is proportional to molecular weight, R is a $C_1$–$C_{20}$ alkyl radical and X is a cosmetically acceptable anion such as a halide, sulfate or carboxylate, which can be made by quaternizing and then polymerizing vinylpyridine in a manner known per se:

poly (methacrylamidopropyltrimethylammonium chloride), hereinafter referred to as "Clairquat-1", which is made by polymerizing in a manner known per se the corresponding monomer sold by Texaco Chemicals under the name MAPTAC and which polymer is said to be constituted of repeating units of the moiety:

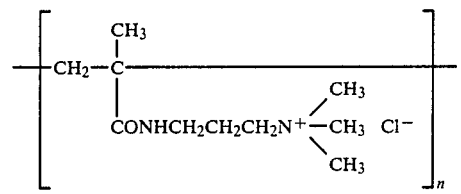

where n is a number which is proportional to molecular weight.

quaternized poly(vinylamine), hereinafter referred to as "QPVAMINE", which can be made by quaternizing and polymerizing vinylamine in a manner know per se, and which is believed to be constituted from repeating units of the moiety:

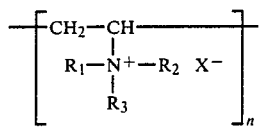

where $R_1$, $R_2$ and $R_3$ are the same or different and represent $C_1$–$C_{20}$ alkyl groups, and X is a cosmetically acceptable anion such as halide, sulfate or carboxylate; and quaternized poly(ethyleneimine), hereinafter referred to as "QPEMINE", which can be prepared by quaternizing and polymerizing ethyleneimine in a manner known per se, and which is believed to be constituted from n repeating units of the monomeric moiety:

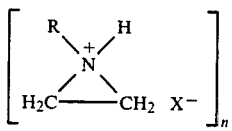

where n is a cardinal number which is proportional to the molecular weight of the polymer, R is a $C_1$-$C_{20}$ alkyl group, and X is a cosmetically acceptable anion such as a halide, sulfate or carboxylate.

Quaternium-19, a polymer of hydroxyethyl cellulose reacted with epichlorohydrin and then quaternized with trimethylamine (sold by Union Carbide Corporation under the name Polymer JR-400). Some cationic polymers, such as quaternium 19, can be especially advantageously used in combination with other cationic polymer, such as those enumerated above.

In the foregoing enumeration of specific cationic polymers, the chemical structures are those that were given by the respective manufacturers or were otherwise postulated. Therefore the formulae does not necessarily accurately represent the actual structures of the respective monomeric units that constitute the particular cationic polymer. For example, it was recently learned that the manufacturers of two of the cationic polymers in the foregoing listing changed their views about the formulae which they initially provided for their respective cationic polymer without changing their respective products. The new structural representations, as provided by their respective manufacturers, appear in this application with respect to those two cationic polymer products. It is for that reason that we do not wish to be bound to any specific structural representation of any cationic polymer product herein, but in each case view the manufacturer's trademark, the CTFA designation and any chemical name (the latter usually based on what was done to a precursor to obtain the end product), to be of equal significance in defining each cationic polymer.

As it can be readily appreciated, the term "cationic polymer" is not restricted to homopolymers, but copolymers of multiple monomers are intended to be included in the meaning of the term.

Those specific cationic polymers that were enumerated above were found to perform, with one exception over a wide range of molecular weights between about 4,000 to about 550,000; most of them suitably from about 20,000 to about 100,000. The only exception that was found so far is Onamer which is effective at a molecular weight between about 1,000 and about 3,000. The manner of determining and expressing the molecular weight makes no difference in this case.

The mechanism of the durable conditioning reaction obtained in accordance with the present invention is not clearly understood. We believe that initially the positively charged sites of the cationic polymer product component of the composition forms a bond with the negatively charged sites of the hair. Up to this point the assumed mechanism is similar to the known, normal conditioning of hair when positively charged monomeric or polymeric quaternary amines are employed for conditioning. While we postulate that, in accordance with our invention, the remaining free positive charges of the cationic polymer react in the presence of hair with the anionic surfactant residue from a preceding shampoo or with such a surfactant from a subsequent shampoo to form the durable conditioning complex on the hair which remains attached to the hair and conditions it through several shampoos without need for reapplication each time, we do not which to be bound by this speculative assertion. Furthermore, the ionic interaction with an anionic shampoo is believed to be just one of a plurality of molecular processes, some of which might even compete with each other. For example, the fact that the functioning of the composition of the present invention is sensitive to effective concentration limits of the cationic surfactant and the cationic polymer seems to support that belief. Thus, it is believed that the cationic polymer tends to balance out the negative charge of the hair and the silicone, but above its effective concentration limit it tends to make the charge excessively positive and thus cause a flyaway hair condition. Furthermore, it is believed that while the cationic surfactant up to its effective concentration limits primes the hair surface and promotes the deposition of the conditioning silicone from the emulsion, above the effective concentration limit it tends to re-emulsify the deposited silicone. Again, as above, we do not wish to be bound by our speculation as to the phenomena that may take place in the use of the composition of the present invention.

The effective amount of the water soluble cationic polymer contained in the formulation will depend on the particular results that are desired and the identity of the polymer. Ordinarily, this will constitute between from about 0.005 to about 1% by weight based on the total weight of the aqueous composition.

Similarly, the effective amount of the cationic surfactant can suitably vary between from about 0.1 to about 1.5% by weight, based on the composition. It is to be understood, however, that the effective concentration could have a different maximum in the case of different materials.

The amount of amino-functional silicone polymer in emulsion form that will be incorporated in the present hair conditioning composition can also vary somewhat. Usually, however, this will comprise, based on the silicone content of the composition, from about 0.2% to about 10% by weight based on the total weight of the composition and preferably from about 1% to about 4%.

Although the cationic polymer, cationic surfactant and the silicone polymer are the essential, active ingredients of the present compositions, the compositions contemplated by the present invention can also contain other ingredients which may serve to improve the organoleptic character of the product or its ease of application. Thus, it is within the purview of this invention to incorporate such materials as fragrance, thickening agents, opacifiers, emulsifying assisdents, etc. in the compositions of this invention.

The carrier for delivering the compositions of the present invention will generally be an aqueous vehicle. This may take any of a variety of forms e.g. solutions, aqueous emulsions, aqueous gels, etc. As used herein, the term aqueous carrier is intended to include the cases wherein water is essentially the only material that constitutes the vehicles as well as those cases wherein the water is mixed with substantial quantities of other ingredients e.g. solvents, thickening agents, emulsifying agents, gelling agents, etc.

The compositions of the present invention can be applied to hair in any suitable manner. One typical procedure involves applying the conditioning composition, such as described in Example 1 below to freshly shampooed hair, working it gently into the hair mass, leaving the said composition on hair for one to five minutes and rinsing the hair thoroughly with water prior to combing. The amount of the conditioning composition applied to hair can vary but, in general, should not be less than 1% of the hair weight and usually does not exceed 20% of the hair weight.

The following Examples are given to further illustrate the present invention. It is to be understood, however, that the invention is not limited thereto.

The compositions of Examples I–VI when applied to previously shampooed hair, were found to provide an excellent reduction of combing force (i.e. conditioning) even following three shampoos after application.

EXAMPLE I

| Ingredient | % by weight |
| --- | --- |
| silicone polymer (amodimethicone) in form of aqueous emulsion (cationic emulsion-929) | 1.6 |
| quaternium-40 | 1.6 |
| hydroxyethyl cellulose | 1.5 |
| citric acid | 0.5 |
| water QS to | 100.0 |

EXAMPLE II

| Ingredient | % by weight |
| --- | --- |
| cationic emulsion-929 | 1.6 |
| polyvinyl allyl pyridinium sulfate | 1.6 |
| hydroxyethyl cellulose | 1.5 |
| citric acid | 0.5 |
| water QS to | 100.0 |

EXAMPLE III

| Ingredient | % by weight |
| --- | --- |
| cationic emulsion-929 | 1.6 |
| quaternium-40 | 0.8 |
| polyvinyl methyl pyridinium iodide | 0.8 |
| hydroxyethyl cellulose | 1.5 |
| citric acid | 0.5 |
| water QS to | 100.0 |

EXAMPLE IV

| Ingredient | % by weight |
| --- | --- |
| cationic emulsion-929 | 2.0 |
| onamer | 1.5 |
| hydroxyethyl cellulose | 1.5 |
| water QS to | 100.0 |

EXAMPLE V

| Ingredient | % by weight |
| --- | --- |
| cationic emulsion-929 | 1.75 |
| stearyl alcohol | 1.6 |
| glyceryl monosterate | 1.5 |
| mineral oil | 0.8 |
| quaternium-41 | 0.4 |
| propyl paraben | 0.5 |
| water QS to | 100.0 |

EXAMPLE VI

| Ingredient | % by weight |
| --- | --- |
| cationic emulsion-929 | 1.75 |
| stearyl alcohol | 1.4 |
| glyceryl monosterate | 1.5 |
| stearalkonium chloride | 0.07 |
| quaternium-19 | 0.05 |
| clairquat-1 | 0.17 |
| propyl paraben | 0.4 |
| water QS to | 100.0 |

The conditioning efficacy and durability is further illustrated in the following experiment, the normal, Caucasian hair being used as the test substrate.

Swatches of intact Caucasian hair were shampooed with Herbal Essence Shampoo in accordance with the instructions present on the label. The ratio of the amount of shampoo to weight of hair and quality of water used for rinsing after shampooing were all maintained so as to simulate conditions on the head. After rinsing, the conditioning material of Example I above was applied to hair (0.1 g of each product per 1 g of hair). It was worked in for 30 seconds and left on the hair for an additional minute after which time the hair was rinsed and combed. The combing measurements were performed by the procedure described in the aforementioned article by Garcia et al. The test essentially involves passing of a hair tress through a comb attached to a strain gauge which in turn is connected to a recording device. Force is expended to accomplish the passage of the tress through the comb, and the maximum force read off the recorded in the objective measure of combing ease.

Having determined the combing properties of hair after shampooing and conditioning treatments, the swatches were shampooed five times and again tested for combing. The results of combability tests are summarized in Table I below. In the Table, the "Maximum Combing Force" is expressed in units of Gram Force (G). The higher the values, the harder it was to comb the hair.

TABLE I

Effect of Conditioning on Combing Ease

| Procedure # | Treatment | Maximum Combing Force (G) |
| --- | --- | --- |
| 1 | Shampooing | 80 |
| 2 | Proc. (1) followed by treatment with conventional conditioner | 42 |
| 3 | Proc. (2) followed by 5 shampoos | 97 |
| 4 | Proc. (1) followed by treatment with composition for Example I without the quaternium-40 | 29 |
| 5 | Proc. (4) followed by 5 shampoos | 60 |
| 6 | Proc. (1) followed by treatment with composition from Example I | 12 |
| 7 | Proc. (6) followed by 5 shampoos | 18 |

Even better durability of conditioning properties was obtained with compositions of Example IV. Again, freshly shampooed, brown Caucasian hair tresses were used in the experiment. The results are given in Table II below.

TABLE II

Effect of Conditioning on Combing Ease

| Procedure # | Treatment | Maximum Combing Force (G) |
|---|---|---|
| 1 | Shampooing | 92 |
| 2 | Proc. (1) followed by treatment with composition of Example IV without the polymer | 19 |
| 3 | Proc. (2) followed by 10 consecutive shampooings | 79 |
| 4 | Proc. (1) followed by treatment with composition of Example IV | 11 |
| 5 | Proc. (4) followed by 10 consecutive shampooings | 16 |

Although the invention has been described with reference to specific forms thereof, it will be understood that many changes and modifications may be made without departing from the spirit of this invention.

We claim:

1. A hair conditioning composition comprising:
   (a) from about 0.2 to about 10% by weight of an amino functional silicone polymer in aqueous emulsion;
   (b) an effective amount for increasing the combability of hair, of a cationic surfactant-emulsifier containing at least one long chain fatty acid residue, such residue containing between 12 and 18 carbon atoms; and
   (c) an effective amount for increasing the combability of hair and for improving the durability of the conditioning effect, of at least one cationic polymer; in
   (d) an aqueous carrier.

2. The hair conditioning composition of claim 1, wherein said amino functional silicone polymer is amodimethicone.

3. The hair conditioning composition of claim 1, wherein said cationic surfactant-emulsifier is at least one of tallowtrimonium chloride and stearalkonium chloride.

4. The hair conditioning composition of claim 1, 2 or 3, wherein said cationic polymer is at least one of quaternium-40, quaternium-41, onamer, quaternized poly-4-vinyl pyridine, poly(methacryl-amidopropyltrimethyl ammonium chloride), quaternized poly(vinylamine), quaternized poly(ethyleneimine); and quaternium-19.

5. The hair conditioning composition of claim 2, wherein said cationic surfactant-emulsifier is at least one of tallowtrimonium chloride and stearalkonium chloride, and said effective amount of said cationic surfactant-emulsifier is from about 0.1 to about 1.5% by weight based on the composition, and said cationic polymer is at least one of quaternium-40, quaternium-41, onamer, quaternized poly-4-vinyl pyridine, poly(methacryl-amidopropyltrimethyl ammonium chloride), quaternized poly(vinylamine), quaternized poly(ethyleneimine); and quaternium-19, and said effective amount of said cationic polymer is from about 0.05 to about 1% by weight, based on the composition.

6. A process for conditioning hair which comprises applying the composition of claims 1 or 5 to hair and shampooing the hair with an anionic surfactant either before or after the application of said composition.

* * * * *